United States Patent
Kurz

(10) Patent No.: US 7,509,880 B2
(45) Date of Patent: Mar. 31, 2009

(54) FLUID FLOW METER BODY WITH HIGH IMMUNITY TO INLET/OUTLET FLOW DISTURBANCES

(75) Inventor: Jerome L. Kurz, Carmel Valley, CA (US)

(73) Assignee: Los Robles Advertising, Inc., Monterey, CA (US)

(*) Notice: Subject to any disclaimer, the term of this patent is extended or adjusted under 35 U.S.C. 154(b) by 0 days.

(21) Appl. No.: 10/590,160

(22) PCT Filed: Mar. 4, 2005

(86) PCT No.: PCT/US2005/007214

§ 371 (c)(1),
(2), (4) Date: May 2, 2007

(87) PCT Pub. No.: WO2005/086730

PCT Pub. Date: Sep. 22, 2005

(65) Prior Publication Data

US 2008/0034862 A1   Feb. 14, 2008

Related U.S. Application Data

(60) Provisional application No. 60/550,466, filed on Mar. 5, 2004.

(51) Int. Cl.
*G01P 5/06* (2006.01)
(52) U.S. Cl. .................................................. 73/861.85
(58) Field of Classification Search .............. 73/861.63, 73/861.61, 861.64
See application file for complete search history.

(56) References Cited

U.S. PATENT DOCUMENTS

| 5,127,173 | A  | * | 7/1992 | Thurston et al. | ............... | 73/202 |
| 6,612,187 | B1 | * | 9/2003 | Lund | ....................... | 73/861.04 |
| 6,732,596 | B2 | * | 5/2004 | Delajoud | .................. | 73/861.61 |

* cited by examiner

*Primary Examiner*—Jewel Thompson
(74) *Attorney, Agent, or Firm*—Patent Law Group LLP; David C. Hsia

(57) ABSTRACT

Method and device are provided for accurately measuring fluid flow in a conduit. A fluid flow meter conditioning body, in-line with the conduit, conditions the fluid flow so as to provide a flattened and invariant fluid velocity profile. The device provides high immunity to upstream and downstream non-uniform fluid velocity profiles. Fluid diffusers adapt the device to different conduit sizes, eliminate field welding and conduit fittings. In a preferred embodiment thermal convection mass flow sensors and circuitry are used to further improve the accuracy of the measurement of the fluid flow.

19 Claims, 4 Drawing Sheets

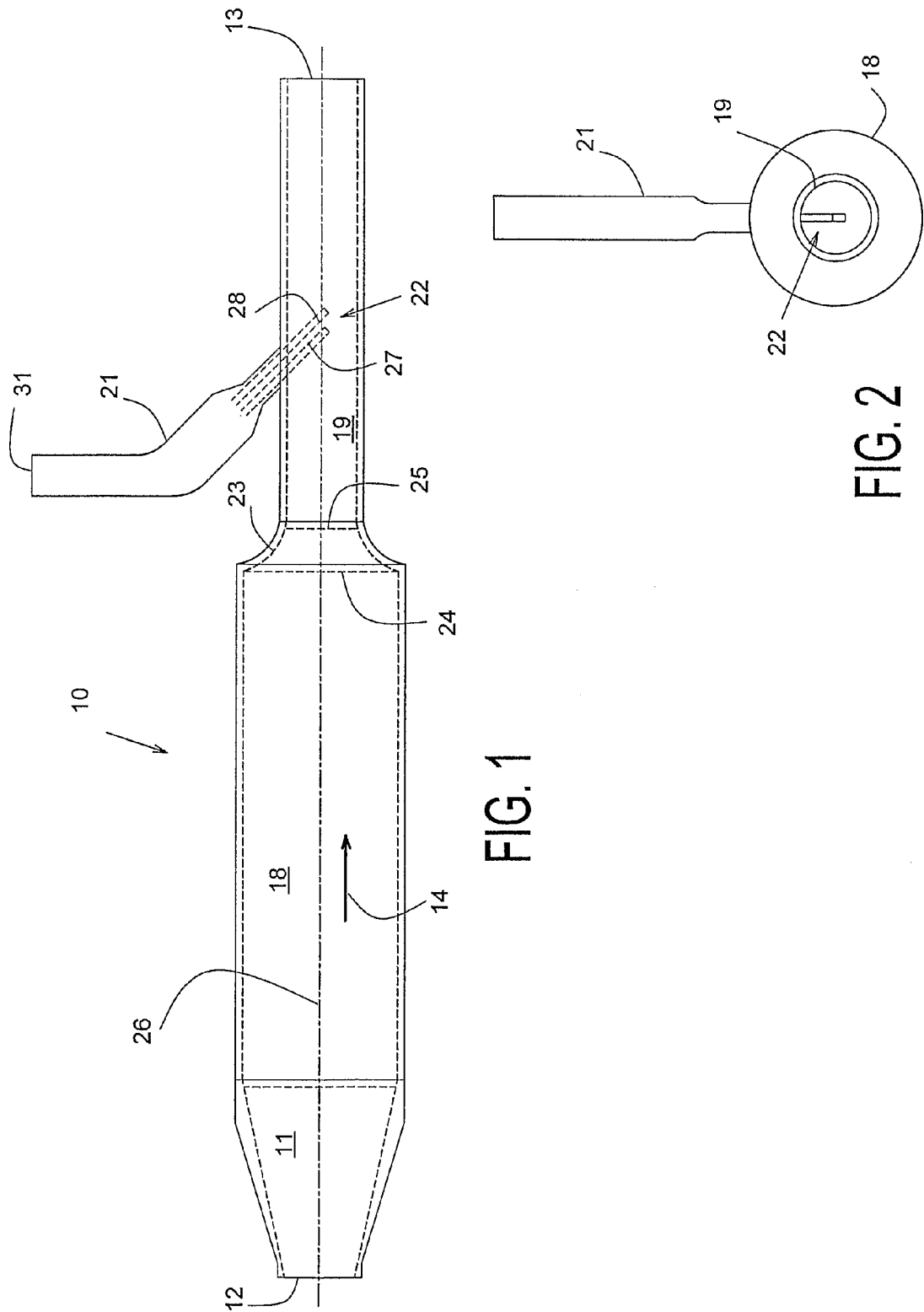

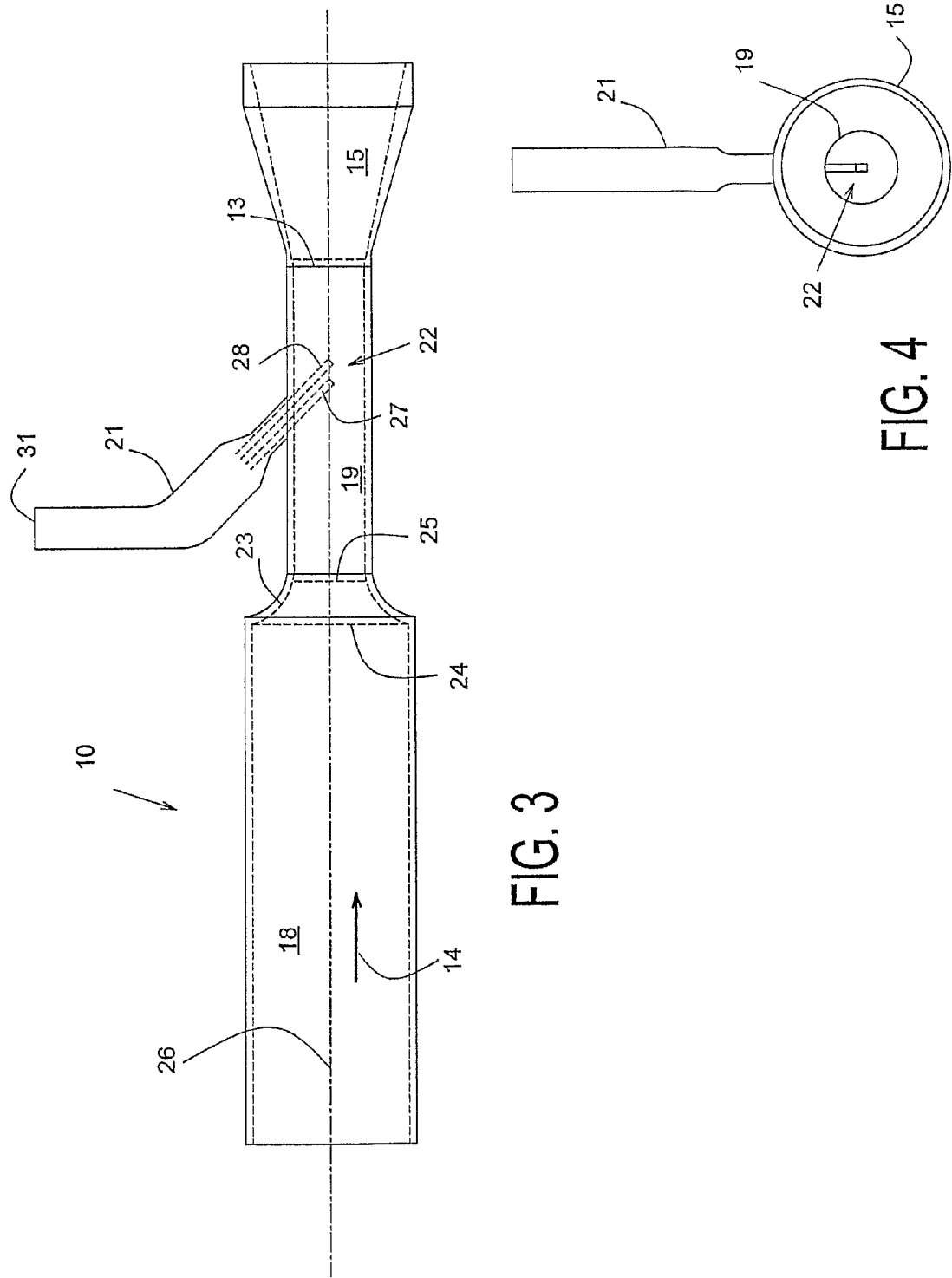

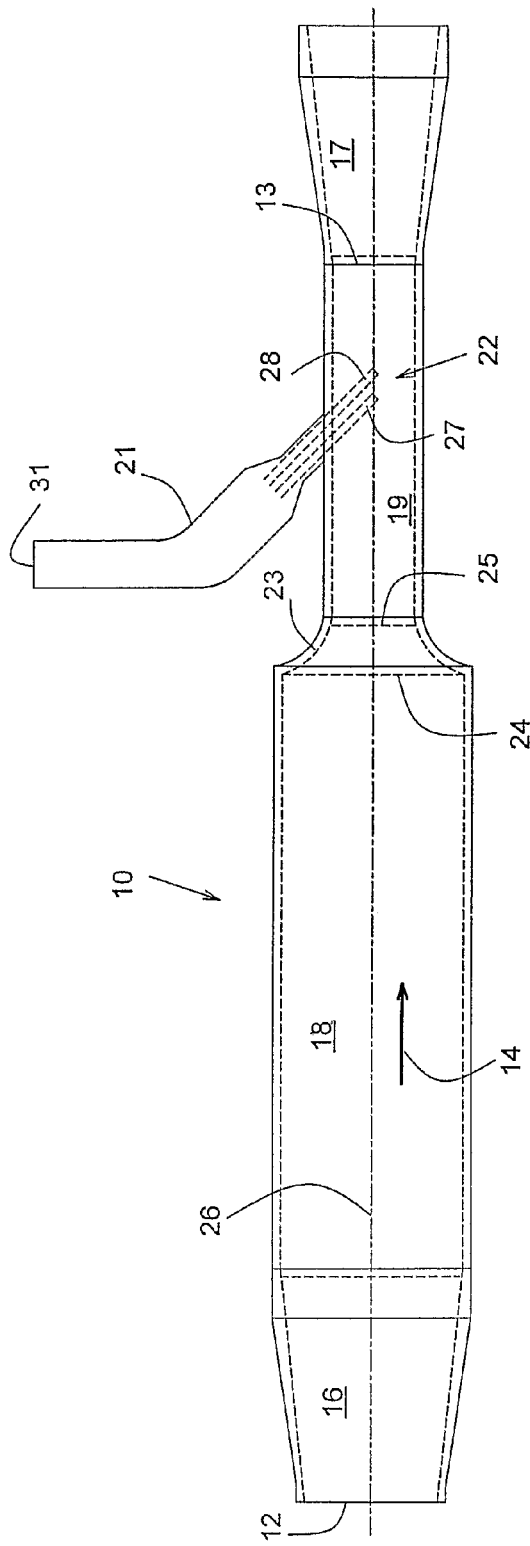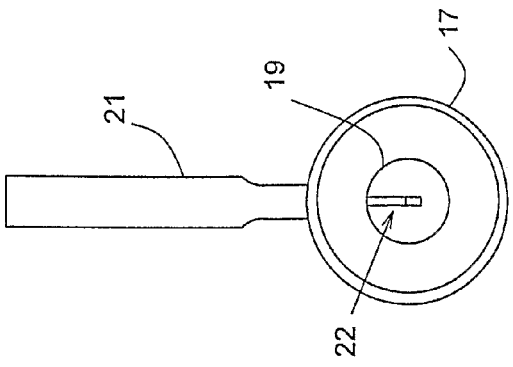
FIG. 5
FIG. 6

FLUID FLOW METER BODY WITH HIGH IMMUNITY TO INLET/OUTLET FLOW DISTURBANCES

This application claims the benefit of U.S. Provisional Application No. 60/550,466, filed Mar. 5, 2004.

FIELD OF THE INVENTION

The present invention is a method and a device for use in conditioning a fluid for measuring flow in a conduit.

BACKGROUND OF THE INVENTION

Accurate measurement of the flow of fluids in a conduit is of extreme importance in many industries. Many devices and processes have been developed over the years to try to obtain more accurate measurements of fluid flow. One method, which is widely known, is the pressure differential type in which a pressure differential produced as the fluid passes through a restriction in a conduit is used to calculate fluid flow. Another method is a pitot tube method.

Another known method, used to measure fluid flow, is generally referred to as a "thermal convection mass flow method". There are two widely-known types of thermal mass flow meters, energy balance and convection. Energy balance flow meters generally use a small diameter capillary tube having a large length/diameter ratio to ensure fully developed fluid velocity and temperature profiles. The temperature of the fluid is measured at the inlet and outlet, and a constant source of heat is added to the fluid stream. The temperature gain is a function of the specific heat of the fluid and the mass flow, and follows the First Law of Thermodynamics. These devices are generally used for small clean gas flows with modest flow and temperature ranges.

In a second type of thermal mass flow meters, thermal convection mass flow meters, a heated sensor is inserted into a fluid stream. Since convective heat transfer is dependent on the fluid transport properties and the temperature difference between the heated sensor and the fluid, a temperature sensor is incorporated into the mass flow sensor and is used for temperature compensation. Two basic types of thermal convection mass flow sensor electronic circuits are in general industrial use with this type of meter: Constant Power Anemometer (CPA), and Constant Temperature Anemometer (CTA). A Constant Power Anemometer (CPA) provides constant electrical power to a resistance element. A temperature sensor is attached to the heater and is heated by conduction from the heater element. The difference between the temperature of the heated sensor and the ambient fluid temperature sensor is measured. The temperature difference is large at a low velocity and small at a high velocity. The temperature difference signal is conditioned to be linear with the mass velocity, and ambient temperature compensation is usually accomplished with analog signal processing. Constant power anemometers are slow to respond to changes in velocity and temperature because of the thermal inertia of the sensors; they do not have a stable "zero" because of the increased free convection caused by the high sensor temperature at zero flow; and unless specially corrected, they have a limited range of temperature compensation (±30° F.). Most CPA's use three sensors to provide the power, heated sensor temperature and ambient sensor temperature, and are very sensitive to non-axial velocity components because of the non-symmetric shape of the sensors.

The other basic type of thermal convection mass flow sensor electronic circuit is the Constant Temperature Anemometer (CTA). In this instrument, a single Resistance Temperature Detector (RTD) sensor is operated by a solid-state feedback control circuit to maintain a constant temperature difference between a heated sensor and the process fluid temperature, which is measured by a second Resistance Temperature Detector (RTD) sensor. The amount of electrical power needed to maintain this temperature difference is the measured output variable. As the fluid temperature changes, the CTA control circuit maintains a nearly constant "overheat" temperature difference between the heated sensor and the ambient fluid temperature. The CTA circuit has a significant advantage over the CPA circuit because temperature compensation can be made for the temperature difference and the rate of change of the temperature difference. The CTA has several advantages over the CPA, these advantages are:

A high level output is obtained. In most cases, a power transfer ratio of 9:1 from zero velocity to 200 SFPS is obtained.

Only two sensors are needed, rather than three as used in a CPA.

CTA's have a much faster response to velocity changes than CPA's because only the outer surface of the heated element must be heated. Thus, CTA's have a velocity time constant of about 1 second and are 5 to 10 times faster than the time constant if used as a temperature sensor.

CTA'S, if properly designed, have a much smaller time constant than CPA's for fast changes in ambient fluid temperature.

CTA's are much less sensitive to the angle of velocity approach because the two sensors are circular and symmetrically mounted.

In order to obtain accurate measurements with a fluid flow measuring device, it is important to have an accurate and dependable sensor and related control circuit, such as described above, and to have that sensor located in the fluid stream at a location which is representative of the flow of the fluid. Ideally, having a fluid velocity profile which is flat would simplify obtaining such representative fluid flow; however such fluid velocity profile is not normally encountered, especially in sections of conduit upstream and downstream of pipe size changes, elbows, valves and other flow disturbances.

OBJECTS OF THE INVENTION

It is an object of the present invention to provide an in-line fluid flow meter conditioning body coupled with a velocity sensor to accurately measure the flow of a fluid in a conduit.

It is a further object of the present invention to provide a fluid flow meter conditioning body which provides accurate measurements even when located upstream or downstream of velocity profile disturbing factors.

It is still a further object of the present invention to provide a fluid flow meter conditioning body which has a fast response to fluid temperature and velocity changes.

It is yet a further object of the present invention to provide a minimum end-to-end pressure loss.

It is yet a further object of the present invention to provide a flexibility to adapt to a user's conduit by including flow diffusers

SUMMARY OF THE INVENTION

The present invention is an in-line fluid flow conditioning device, having a fluid flow meter conditioning body, for placement in a fluid conveying conduit. The fluid flow meter conditioning body has an elongated inlet flow section, an elongated flow measurement section for containing a thermal mass flow sensors, or other velocity sensing device, and a flow nozzle intermediate the inlet flow section and the flow measurement section. The inlet flow section, the flow nozzle and the flow measurement section are arranged along a longitudinal axis, and the inlet flow section, the flow nozzle and the flow measurement section communicate for fluid flow in a direction from the inlet flow section toward the flow measurement section. The cross section of the inlet flow section, in a plane perpendicular to the longitudinal axis, is greater than a comparable cross section of the flow measurement section. The method of the invention conditions the fluid velocity profile at the location of the velocity sensor so that the fluid has a substantially flattened and invariant velocity profile at the point of flow measurement.

Viewed in another aspect, the present invention provides, in a method for measuring fluid flow in an apparatus, the improved step of conditioning the fluid flowing through the apparatus so that the fluid has a substantially flattened fluid velocity profile at the point of measurement.

In a preferred embodiment, the apparatus comprises a fluid flow meter conditioning body.

Preferably, the fluid flow meter conditioning body has an inlet section connected to an adjacent conduit, and the inside diameter of the conduit is matched to the inside diameter of the inlet section.

In an alternate embodiment, the fluid flow meter conditioning body has a flow measurement section, and the diameter of the flow measurement section is matched to the inside diameter of the conduit.

These and other objects of the present invention will become apparent from a reading of the following specification taken in conjunction with the enclosed drawings.

BRIEF DESCRIPTION OF THE DRAWINGS

The invention will become more readily apparent from the following description of a preferred embodiment thereof, shown, by way of example only, in the accompanying drawings, wherein:

FIG. 1 is a side view of an in-line fluid flow meter conditioning body of the invention having an upstream flow diffuser;

FIG. 2 is an end view from an outlet end of the in-line fluid flow meter conditioning body of FIG. 1;

FIG. 3 is a side view of the in-line fluid flow meter conditioning body of the invention having a downstream flow diffuser;

FIG. 4 is an end view from an outlet end of the in-line fluid flow meter conditioning body of FIG. 3;

FIG. 5 is a side view of the in-line fluid flow meter conditioning body of the invention having an upstream flow diffuser and a downstream flow diffuser;

FIG. 6 is an end view from an outlet end of the in-line fluid flow meter conditioning body of FIG. 5;

DETAILED DESCRIPTION OF THE INVENTION

Figure 7:
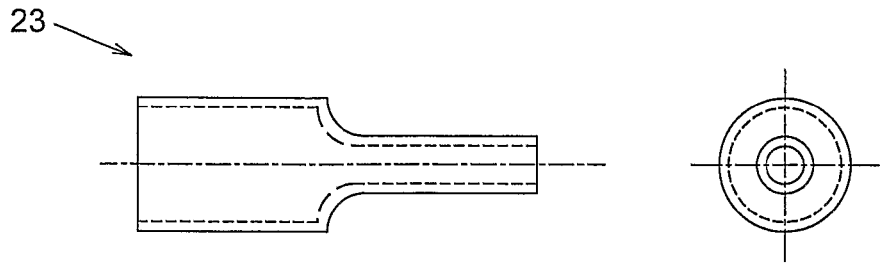
FIG. 7 is side and end views of a flow nozzle of the invention having a radius transition.

An in-line fluid flow meter conditioning body of the invention is illustrated in FIG. 1 at reference numeral 10. The body 10, shown in FIG. 1, is configured with an inlet diffuser 11, so as to provide an inlet 12 and an outlet 13 having like diameters for placement in a conduit for which the rate of fluid flow is to be measured. The flow of the fluid through the device is in the direction indicated by arrow 14. The fluid flow meter conditioning body, along with the inlet diffuser is for placement in a conduit. Preferably, the diameter of the conduit is the same diameter as that of the inlet and outlet 12 and 13.

In other arrangements of the fluid flow meter conditioning body 10 of the invention, shown in FIGS. 3 and 5, other inlet and outlet diffusers are arranged with the fluid flow meter conditioning body in order to provide the same inlet and outlet diameter, which preferably is the same size as that of the conduit in which the fluid is flowing. In FIG. 3 an outlet flow diffuser 15 is provided, and in FIG. 5 an inlet flow diffuser 16 and an outlet flow diffuser 17 are provided. The above-mentioned flow diffusers are described in more detail below.

The fluid flow meter conditioning body 10, as shown in FIGS. 1, 3, and 5, is made up of an inlet section 18, a flow measurement section 19 and flow nozzle 23 through which the fluid flows. Additionally, a sensor assembly 21 is attached to flow measurement section 19. Sensors of the device 22, are supported by the sensor assembly 21.

As mentioned above the accuracy of fluid flow measurements is very much dependent on the location of the sensors and the velocity profile of the fluid stream at that location. The present fluid flow meter conditioning body is arranged to minimize the influence of upstream and downstream pipe size changes, elbows, valves and other factors causing flow disturbances. Features of the fluid flow meter conditioning body eliminate the need for adapters, field welding, and other measures which could lead to undesired flow characteristics. Also the positioning of the sensors is such as to provide the most accurate measurements.

A main function of the fluid flow meter conditioning body is to condition the flow of the fluid so that the fluid, at the point of measurement, has a substantially flattened velocity profile. The fluid flow is made to be invariant, that is, the velocity profile does not change appreciably over a wide range of flows, temperatures, and other varying conditions. To achieve such profile, the inlet section 18 of the fluid flow meter conditioning body 10 is sized to have a diameter about two times larger than a diameter of the flow measurement section 19. Such sizing provides a cross-sectional area ratio of the two sections of about 4:1 or a beta of 0.5. Although a beta of 0.5 is preferred, a range of 0.3 to 0.7 is possible, 0.3 being better than 0.7.

Figure 8:
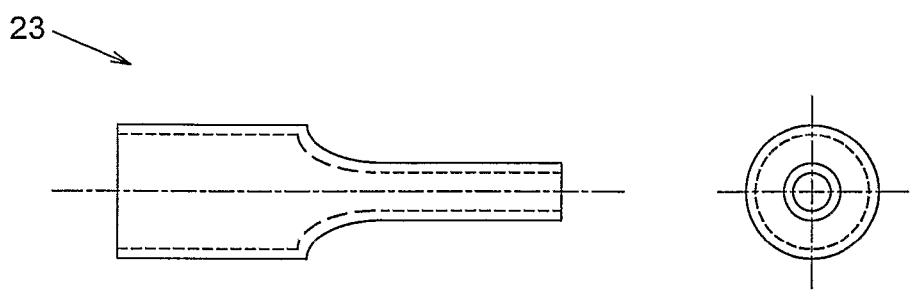
FIG. 8 is side and end views of a flow nozzle of the invention having an elliptic transition.
Figure 9:
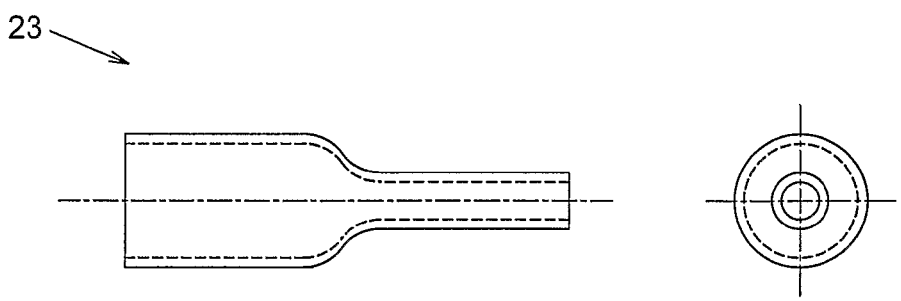
FIG. 9 is side and end views of a flow nozzle of the invention having a bell shape transition.
Figure 10:
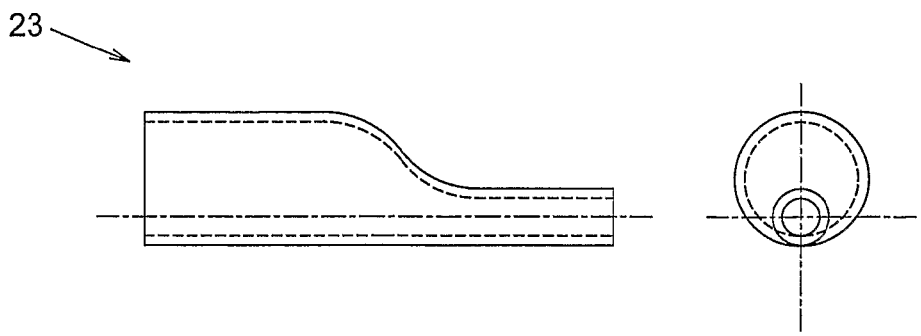
FIG. 10 is side and end views of a flow nozzle of the invention having an eccentric bell-shaped transition.

An internal surface of the transition section between inlet section 18 and flow measurement section 19, forms a flow nozzle 23 having an inlet 24 with a cross section corresponding to that of the inlet section 18, and an outlet 25 with a cross section corresponding to that of the flow measurement section 19. Between the inlet and outlet, 24 and 25, the internal surface of the flow nozzle is preferably concentric about the central longitudinal axis 26 of the flow meter conditioning body, and when viewed in a plane containing central longitudinal axis 26, has an arc, an elliptical or a bell shape. The internal surface of the flow nozzle is arranged to contact the internal surfaces of the inlet section 18 and the flow measurement section 19, without any gap or ridge which would interrupt the fluid flow. Although a concentric nozzle is preferred, an eccentric nozzle can be used, when necessary, such as for allowing for liquid formed on the bottom of a substantially horizontal conduit to be drained away. FIGS. 7-10 show possible configurations for the nozzle. FIG. 7 shows a nozzle having a radius transition, with the radius being 0.5 times the difference in the diameter of the inlet and the outlet. FIG. 8 shows a nozzle having an elliptic transition. FIG. 9 shows a nozzle having a bell shaped transition. FIG. 10 shows a nozzle which is eccentric.

In a preferred embodiment, the length of inlet section 18 is greater than about 6 times its inside diameter, and the length of the flow measurement section is greater than about 6 times its inside diameter. The length of the flow nozzle, along longitudinal axis 26, is at least about 0.5 to 2.0 times the difference in the diameters of the nozzle inlet 24 and the nozzle outlet 25.

Preferably, the flow sensor 22 of the measuring device is mounted, with use of sensor assembly 21, to be a distance of about 1.5-3.5 times the diameter of the flow measurement section 19 from the inlet of the flow measurement section. In a preferred embodiment a constant temperature anemometer (CTA) type circuit is used with the sensor, however, any velocity sensor having substantially a single-point measuring portion can be used. One example is a pitot tube. As shown in FIG. 1 the CTA type circuit utilizes two sensor elements 27 and 28, which are aligned with each other, and which have their measuring portion ends staggered along a longitudinal axis of the sensor. In a preferred embodiment a midpoint between the ends is positioned on central longitudinal axis 26 of the flow measurement section as best viewed in FIGS. 2, 4, and 6 at a distance, which is described above, downstream from the nozzle. Leads of the sensor exit the fluid flow meter conditioning body through end 31 of the sensor assembly 21 and are preferably connected to CTA sensor circuitry (not shown) which uses a modified Wheatstone Bridge to accurately measure the electrical power required to maintain the temperature difference, as discussed above. Use of such electrical power, current, or voltage measurement to determine thermal mass flow rate is known in the art.

As mentioned above the accuracy of the fluid flow values is highly dependent on the velocity profile of the fluid stream. To promote the desired flattened profile, in addition to the above-described fluid flow meter conditioning body, communication of such fluid flow meter conditioning body with the conduit, into which the body is installed, is of importance. Ideally the inside diameter of the conduit matches either the inside diameter of the inlet section 18 (FIG. 3) or the flow measurement section 19 (FIG. 1). However, in view of the relationship of the inside diameter of the inlet section to the inside diameter of the flow measurement section (about 2:1 diameter ratio), it is necessary to use either an inlet diffuser 11 or an outlet diffuser 15, as shown in FIGS. 1 and 3, respectively. Additionally, if the inside diameter of the conduit does not match either the inlet section inside diameter or the flow measurement section inside diameter, the use of both an inlet flow diffuser 16 and outlet flow diffuser 17, as shown in FIG. 5, is necessary. In situations having very high fluid velocity, it is preferred to use an inlet flow diffuser to connect a conduit with an inlet flow section of sufficient diameter to significantly lower the fluid velocity for optimum performance. Use of the device in substantially any size conduit is possible.

An inlet flow diffuser 11, 16 is configured to have an inlet diameter matching the conduit, and an outlet diameter matching the inlet section 18. A preferred length of the inlet flow diffuser is such that a 7 degree half-angle expansion is obtained. A 6 degree to 9 degree half-angle is possible in practice of the invention. The transition between the inlet and outlet of the diffuser is preferably uniform. The inner wall of the inlet flow diffuser is configured so that no gap or ridge is present where its inner wall meets the inner walls of the conduit or the inlet section.

An outlet flow diffuser 15, 17 is configured to have an inlet diameter matching the flow measurement section 19, and an outlet diameter matching the inside diameter of the conduit. A length of the inlet flow diffuser preferably is such that a 7 degree half-angle expansion is obtained. A 6 degree to 9 degree half-angle is possible in practice of the invention. The transition between the inlet and outlet of the diffuser is preferably uniform. The inner wall of the outlet diffuser is configured so that no gap or ridge is present where its inner wall meets the inner walls of the flow measurement section or the conduit. Although diffusers having a concentric transition are preferred, eccentric diffusers are possible where the drainage of liquid on the bottom of the device, which is installed substantially horizontally, is required. Although not shown, the fluid flow meter conditioning body can be connected to the conduit with use of flanges, threaded sections, or special connectors.

When a fluid flow meter conditioning body 10 is properly sized to a conduit, in which the fluid to be measured is flowing, the inlet flow diffuser, placed upstream of the inlet flow section 18, decelerates the velocity of the fluid thereby allowing the fluid to expand, flow through the flow nozzle, and present an invariant, flat velocity profile to the sensor 22 located in the flow measurement section downstream of the flow nozzle. The outlet flow diffuser, placed downstream of the flow measurement section and flow nozzle, provides a means for recovering a large percentage of the pressure drop across the flow nozzle, thus reducing the pressure drop through the fluid flow meter conditioning body. In a preferred embodiment the fluid flow meter conditioning body is fabricated of stainless steel.

The present invention provides an in-line fluid flow meter conditioning body with exceptional immunity to flow disturbances, requires less upstream and downstream length, conveniently mates to a wide range of pipe sizes, eliminates field welding and fabrication of conduit adapter fittings, has a very low end-to-end static pressure loss and has a very large turn-down velocity ratio. Typical applications include process gas measurement in chemical and petrochemical plants, combustion air measurements for large combustion processes, fuel flow control for burners and fuel cells, and semi-conductor process gas measurements. The present invention is for use with both liquid and gas flows While specific materials, dimensional data, processing and fabricating steps have been set forth for purposes of describing embodiments of the invention, various modifications can be resorted to, in light of the above teachings, without departing from Applicant's novel contributions; therefore in determining the scope of the present invention, reference shall be made to the appended claims.

What is claimed is:

1. A fluid flow meter conditioning body, for placement in-line of a fluid conveying conduit comprising
   an elongated inlet flow section,
   an elongated flow measurement section,
   a velocity sensor extending into a space defined by said flow measurement section, and
   a flow nozzle intermediate said inlet flow section and said flow measurement section for substantially flattening a velocity profile of the fluid at the velocity sensor, wherein
   said inlet flow section, said flow nozzle and said flow measurement section are arranged along a longitudinal axis,
   said inlet flow section, said flow nozzle and said flow measurement section communicate for fluid flow in a direction from the inlet flow section toward the flow measurement section, and
   a cross section of said inlet flow section, perpendicular to said longitudinal axis, is greater than a comparable cross section of said flow measurement section.

2. A fluid flow meter conditioning body, for placement in-line of a fluid conveying conduit comprising
   an elongated inlet flow section,
   an elongated flow measurement section for containing a velocity sensor, and
   a flow nozzle intermediate said inlet flow section and said flow measurement section for substantially flattening a velocity profile of the fluid, wherein:
   said inlet flow section, said flow nozzle and said flow measurement section are arranged along a longitudinal axis, said inlet flow section, said flow nozzle and said flow measurement section communicate for fluid flow in a direction from the inlet flow section toward the flow measurement section, and a cross section of said inlet flow section, perpendicular to said longitudinal axis, is greater than a comparable cross section of said flow measurement section, one of:
- an elongated inlet flow diffuser upstream of said inlet flow section,
- an elongated outlet flow diffuser downstream of said flow measurement section, and
- an elongated inlet flow diffuser upstream of said inlet flow section and an elongated outlet flow diffuser downstream of said flow measurement section, wherein
  - each said diffuser is arranged along said longitudinal axis and communicates with the inlet flow section, the flow nozzle, and the flow measurement section for fluid flow therethrough.

3. The fluid flow meter conditioning body of claim 2, wherein
each inlet diffuser is of a length to obtain a half angle expansion of about 6-9 degrees, and has a uniform transition between its inlet and outlet, and
each outlet diffuser is of a length to obtain a half angle expansion of about 6-9 degrees, and has a uniform transition between its inlet and outlet.

4. The fluid flow meter conditioning body of claim 2, wherein
a central longitudinal axis of an inlet of said flow nozzle is displaced from a central longitudinal axis of an outlet of said nozzle, so as to form an eccentric nozzle, and
a central longitudinal axis of an inlet of each said diffuser is displaced from a central longitudinal axis of an outlet of each said diffuser, so as to form an eccentric diffuser.

5. The fluid flow meter conditioning body of claim 2, wherein said flow nozzle has a beta of between about 0.3 and 0.7.

6. The fluid flow meter conditioning body of claim 5, wherein said flow nozzle has a transition between its inlet and outlet having a profile, in a plane containing said longitudinal axis, which is arc shaped, an elliptically shaped, or bell-shaped.

7. The fluid flow meter conditioning body of claim 1, wherein said flow nozzle has a beta of between about 0.3 and 0.7.

8. The fluid flow meter conditioning body of claim 7, wherein said flow nozzle has a transition between its inlet and outlet having a profile, in a plane containing said longitudinal axis, which is arc shaped, elliptically shaped, or bell-shaped.

9. The fluid flow meter conditioning body of claim 1, wherein
said flow measurement section includes a sensor assembly for supporting said velocity sensor.

10. The fluid flow meter conditioning body of claim 9, wherein
said sensor assembly supports said velocity sensor to be centered on a central longitudinal axis of said flow measurement section at a point along the length of the flow measurement section which is a distance of about 1.5-3.5 times the diameter of the flow measurement section.

11. The fluid flow meter conditioning body of claim 1, wherein
a central longitudinal axis of an inlet of said flow nozzle is displaced from a central longitudinal
axis of an outlet of said nozzle, so as to form an eccentric nozzle.

12. A flow measurement system, comprising
a fluid flow meter conditioning body, for placement in-line of a fluid conveying conduit comprising
an elongated inlet flow section,
an elongated flow measurement section,
a flow nozzle intermediate said inlet flow section and said flow measurement section,
a velocity sensor within said flow measurement section, and
a velocity sensor electronic circuit, wherein
said inlet flow section, said flow nozzle and said flow measurement section are arranged along a longitudinal axis, said inlet flow section,
said flow nozzle and said flow measurement section communicate for fluid flow in a direction from the inlet flow section toward the flow measurement section, and
a cross section of said inert flow section, perpendicular to said longitudinal axis, is greater than a comparable cross section of said flow measurement section.

13. The flow measurement system of claim 12, further comprising one of
an elongated inlet flow diffuser upstream of said inlet flow section,
an elongated outlet flow diffuser downstream of said flow measurement section, and
an elongated inlet flow diffuser upstream of said inlet flow section and an elongated outlet flow diffuser downstream of said flow measurement section, wherein
each said diffuser is arranged along said longitudinal axis and communicates with the inlet flow section, the flow nozzle, and the flow measurement section for fluid flow therethrough.

14. The flow measurement system of claim 12, wherein said velocity sensor is a thermal convection mass flow sensor and said electronic circuit is a constant power anemometer type or a constant temperature anemometer type.

15. The flow measurement system of claim 13, wherein said velocity sensor is a thermal convection mass flow sensor and said electronic circuit is a constant power anemometer type or a constant temperature anemometer type.

16. A method for measuring fluid flow in an apparatus, comprising conditioning a fluid flowing through the apparatus so that the fluid has a substantially flattened fluid velocity profile at a point of measurement.

17. The method of claim 16, wherein the apparatus comprises a fluid flow meter conditioning body.

18. The method of claim 17, wherein the fluid flow meter conditioning body has an inlet section connected to an adjacent conduit, the method further comprising matching the inside diameter of the conduit to the inside diameter of the inlet section.

19. The method of claim 17, wherein the fluid flow meter conditioning body is connected to an adjacent conduit, and wherein the fluid flow meter conditioning body has a flow measurement section, the method further comprising matching the inside diameter of the conduit to the inside diameter of the flow measurement section.

* * * * *